(12) United States Patent
Behague et al.

(10) Patent No.: US 7,503,901 B2
(45) Date of Patent: Mar. 17, 2009

(54) COLLECTION BAG SYSTEM WITH PREFORMED LOOP

(75) Inventors: Maurice Behague, Linselles (FR); Francis Goudaliez, Faches-Thumesnil (FR); Thierry Verpoort, Mouvaux (FR)

(73) Assignee: MacoPharma (FR)

( * ) Notice: Subject to any disclaimer, the term of this patent is extended or adjusted under 35 U.S.C. 154(b) by 237 days.

(21) Appl. No.: 10/749,296

(22) Filed: Dec. 31, 2003

(65) Prior Publication Data

US 2004/0186414 A1 Sep. 23, 2004

(30) Foreign Application Priority Data

Feb. 3, 2003 (FR) .................................. 03 01196

(51) Int. Cl.
 *A61M 39/00* (2006.01)
(52) U.S. Cl. .................... 604/6.07; 604/6.01; 604/6.11; 604/410; 604/905
(58) Field of Classification Search ................ 604/6.01, 604/6.05, 6.07, 6.11, 6.14, 410, 905, 6.1
See application file for complete search history.

(56) References Cited

U.S. PATENT DOCUMENTS

| | | | | |
|---|---|---|---|---|
| 3,916,892 A | * | 11/1975 | Latham, Jr. ................... | 604/83 |
| 4,379,452 A | * | 4/1983 | DeVries ..................... | 604/6.11 |
| 4,385,630 A | * | 5/1983 | Gilcher et al. ................. | 604/31 |
| 4,464,167 A | * | 8/1984 | Schoendorfer et al. ..... | 604/6.07 |
| 4,558,996 A | * | 12/1985 | Becker ........................ | 417/374 |
| 4,596,657 A | * | 6/1986 | Wisdom ...................... | 210/206 |
| 4,608,178 A | * | 8/1986 | Johansson et al. ........... | 210/744 |
| 4,674,962 A | * | 6/1987 | Gardineer ................. | 417/477.3 |
| 4,769,001 A | * | 9/1988 | Prince ........................ | 604/6.07 |
| 4,810,378 A | * | 3/1989 | Carmen et al. .............. | 210/206 |
| 4,821,720 A | * | 4/1989 | Hajduch ..................... | 606/157 |
| 4,823,833 A | * | 4/1989 | Hogan et al. ............ | 137/565.33 |
| 4,824,339 A | * | 4/1989 | Bainbridge et al. ....... | 417/477.2 |
| 4,846,795 A | * | 7/1989 | Minagawa ................... | 604/410 |
| 4,850,995 A | * | 7/1989 | Tie et al. ..................... | 604/6.02 |
| 5,027,478 A | * | 7/1991 | Suhr .......................... | 24/16 R |
| 5,064,358 A | * | 11/1991 | Calari ........................ | 417/475 |
| 5,135,667 A | * | 8/1992 | Schoendorfer .............. | 210/782 |

(Continued)

FOREIGN PATENT DOCUMENTS

EP 1 262 202 12/2002

(Continued)

*Primary Examiner*—Tatyana Zalukaeva
*Assistant Examiner*—Paula L Craig
(74) *Attorney, Agent, or Firm*—Baker Botts L.L.P.

(57) ABSTRACT

The invention concerns a bag system for collecting a biological fluid the system intended for use in a collection machine including a peristaltic pump, the system including, in closed circuit, a fluid collection device, a solution bag containing an anticoagulant and/or preservation solution, and a collection bag intended to receive the fluid collected with the anticoagulant and/or preservation solution added. The collection bag is in fluid communication with the collection device by way of a first tube provided with a connector and with the solution bag by way of a second tube connected to the connector. A device for associating the first and second tubes is provided to allow, between the connector and the association device, the formation of a loop with the second tube, the conformation of the loop being arranged to enable it to be disposed around at least part of a head of a peristaltic pump.

7 Claims, 3 Drawing Sheets

U.S. PATENT DOCUMENTS

| | | | | |
|---|---|---|---|---|
| 5,215,450 A | * | 6/1993 | Tamari | 417/474 |
| 5,224,674 A | * | 7/1993 | Simons | 248/68.1 |
| 5,309,604 A | | 5/1994 | Poulsen | 24/16 R |
| 5,330,448 A | * | 7/1994 | Chu | 604/523 |
| 5,352,371 A | | 10/1994 | Felt | 210/787 |
| 5,387,187 A | * | 2/1995 | Fell et al. | 604/6.02 |
| 5,460,493 A | * | 10/1995 | Deniega et al. | 417/477.2 |
| 5,820,582 A | * | 10/1998 | Keilman | 604/500 |
| 5,868,696 A | | 2/1999 | Giesler et al. | 604/6.12 |
| 5,870,805 A | * | 2/1999 | Kandler et al. | 24/459 |
| 5,891,080 A | * | 4/1999 | Skinkle et al. | 604/6.11 |
| 6,113,554 A | * | 9/2000 | Gilcher et al. | 600/573 |
| 6,186,752 B1 | * | 2/2001 | Deniega et al. | 417/475 |
| 6,565,806 B1 | * | 5/2003 | Grimm | 422/44 |
| 6,641,552 B1 | * | 11/2003 | Kingsley et al. | 604/6.02 |
| 6,736,768 B2 | * | 5/2004 | Felt et al. | 494/60 |
| 2002/0033370 A1 | * | 3/2002 | Bainbridge et al. | 210/782 |
| 2002/0128583 A1 | * | 9/2002 | Min et al. | 604/6.01 |
| 2002/0177799 A1 | * | 11/2002 | Rivera et al. | 604/6.01 |
| 2003/0055396 A1 | * | 3/2003 | Goudaliez et al. | 604/408 |
| 2003/0130645 A1 | * | 7/2003 | Brengle et al. | 604/500 |
| 2004/0106890 A1 | * | 6/2004 | Goudaliez et al. | 604/6.15 |
| 2004/0186408 A1 | * | 9/2004 | Behague et al. | 604/4.01 |

FOREIGN PATENT DOCUMENTS

| | | |
|---|---|---|
| WO | WO 01/85029 | 11/2001 |

* cited by examiner

COLLECTION BAG SYSTEM WITH PREFORMED LOOP

PRIORITY CLAIM

The present application claims priority under 35 U.S.C. §119(d) to French Patent Application Ser. No. 03/01196, filed Feb. 3, 2003.

TECHNICAL FIELD

The invention relates to a bag system for collecting a biological fluid, and a collection machine in which such a system is intended to be used to allow the closed-circuit collection of a biological fluid with an anticoagulant and/or preservation solution added.

In particular the invention may be used where the biological fluid is whole blood collected from a donor in a collection bag.

BACKGROUND OF THE INVENTION

It is recommended that blood be collected in a sterile fashion and have an anticoagulant and/or preservation solution added during collection so as to allow its subsequent use under the best sanitary safety conditions.

A bag system for collecting blood is already known, in particular from the document FR-2 808 693. This system includes means of collecting the fluid, a bag containing an anticoagulant and/or preservation solution for the fluid collected, and a collection bag intended to receive the fluid collected with the anticoagulant and/or preservation solution added.

To allow sterile collection of blood, the collection bag is in fluid communication with the collection means by means of a first flexible tube and with the bag containing the anticoagulant and/or preservation solution by means of a second flexible tube, so as to form a closed-circuit system.

This type of system is intended to be used in a collection machine including a peristaltic pump able to partially compress respectively the first and second tubes so as to allow the simultaneous supply to the collection bag of a controlled proportion blood and anticoagulant and/or preservation solution.

To this end, the operation must in particular dispose part of the second tube around a head of the pump so as to allow the supply of the collection bag with anticoagulant and/or preservation solution by partial compression of an area of the second tube.

In practice, this arrangement proves to be difficult and, in cases where it is not properly carried out, the flow of solution pumped does not correspond to that required. The result is therefore a possible deficit or excess of anticoagulant and/or preservation solution in the collection bag, which is detrimental because this solution must be present in a fixed quantity for the blood collected to be usable in the medical field.

SUMMARY OF THE INVENTION

The aim of the invention is in particular to solve the above drawback by providing a bag system for collecting a biological fluid in closed circuit, the system including, prior to its arrangement in a machine, a preformed loop operable to be disposed around at least part of a head of a peristaltic pump.

To this end, and according to a first aspect, the invention concerns a bag system for collecting a biological fluid, in particular blood, the system intended for use in a collection machine including a peristaltic pump. The system includes, in closed circuit, a collection device, a bag containing an anticoagulant and/or preservation solution for the fluid collected, and a collection bag intended to receive the fluid collected with the anticoagulant and/or preservation solution added. The collection bag is in fluid communication with the collection device by way of a first flexible tube provided with a connector and with the bag containing the anticoagulant and/or preservation solution by way of a second flexible tube connected to the connector. A device for associating the first and second tubes is provided. The association device may be operable to allow the formation of a loop with the second tube between the connector and the collection device. The conformation of the loop may be arranged so it is operable to be disposed around at least part of a head of the peristaltic pump.

Thus the operator should dispose the preformed loop around the head of the peristaltic pump to allow the supply of the collection bag with anticoagulant and/or preservation solution, which facilitates the appropriate placement of the second tube in the pump. Apart from the simplification of handling, the result is a reduction in the risk of faulty positioning and therefore in the risk of obtaining a wrong concentration of anticoagulant and/or preservation solution in the collection bag.

According to one embodiment, the connector is formed by a three-way junction to which respectively the downstream end of an upstream part of the first tube, the upstream end of a downstream part of the first tube and the downstream end of the second tube are connected. The association device is formed by a piece provided with an object for associating the device on the second tube and an object associating the first tube on the piece.

According to another embodiment, the connector and the association device are formed in a single piece. The piece is for example formed by a five-way junction to which there are respectively connected the downstream end of an upstream part of the first tube, the upstream end of a downstream part of the first tube, the downstream end of an upstream part of the second tube, the upstream end of a downstream part of the second tube and the downstream end of the downstream part of the second tube.

According to a second aspect, the invention concerns a collection machine in which a bag system according to the invention is intended to be used to allow the collection in closed circuit of a biological fluid while adding an anticoagulant and/or preservation solution. The machine includes a peristaltic pump provided with a compression head able to move in rotation and a device for placing the loop around part of the head so as to allow the supply of the collection bag with anticoagulant and/or preservation solution by partial compression of an area of the part of the second tube forming the loop.

The machine thus includes a placement device specific to the preformed loop of the bag system, which also contributes to improving the ease of handling and the precision of the placement of the second tube in the machine. In addition, by varying the speed of rotation of the head, it is possible to obtain a given flow of anticoagulant and/or preservation solution, under optimum conditions of sterility.

According to one embodiment, the machine includes a single compression head, the fluid being collected by natural flow, that is to say essentially by venous pressure and gravity, and the anticoagulant and/or preservation solution being pumped so as to be added proportionally and continuously to the blood collected.

According to one embodiment, the placement device includes a groove arranged so as to house the part of the loop which is not disposed around the head, the groove including at least one housing for the connector and/or the association device. In particular, the geometry of at least one housing may be arranged so as to allow locking of the connector and/or of the association device in the groove.

This embodiment limits the sliding of the loop when it is compressed by the head, which makes it possible to obtain better control of the flow inside the second tube, in particular because of improvements in the consistency of the flow.

In a variation, the groove is arranged so as to allow placement of the loop in a single direction, which prevents any risk of error in the orientation of the loop around the head which would result for example in supplying the collection means with the anticoagulant and/or preservation solution.

Other objects and advantages of the invention will emerge during the description which follows with reference to the accompanying drawings.

DETAILED DESCRIPTION

Figure 1:
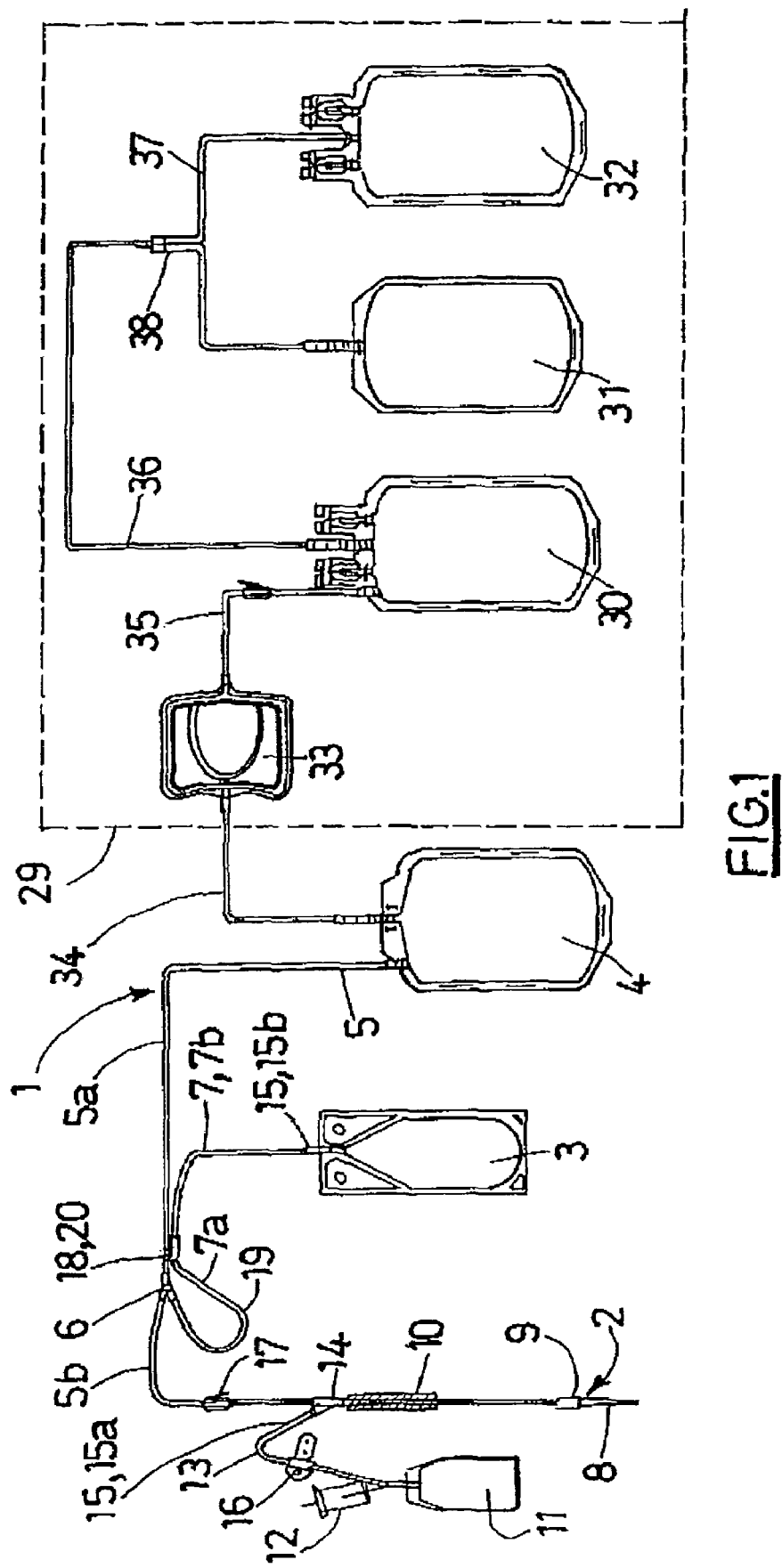
FIG. 1 depicts schematically a bag system according to a first embodiment of the invention.

In relation to FIG. 1, bag system 1 includes collection device 2 for collecting a fluid such as the blood of a donor, solution bag 3 containing an anticoagulant and/or preservation solution for the fluid collected, such as a solution of CDA (citrate dextrose acid) or CPD (citrate phosphate dextrose), and at least one collection bag 4 intended to receive the fluid collected with the anticoagulant and/or preservation solution added. Collection bag 4 is in fluid communication with collection device 2 by way of first tube 5. Bag 3 containing an anticoagulant and/or preservation solution is in fluid communication with first tube 5 at connector 6 by way of second tube 7. First tube 5 and second tube 7 have, for example, identical cross-sections.

All the components of bag system 1 are preconnected so as to form a unitary system which is closed or in closed circuit. The system thus formed is therefore ready to use. In particular, the bag of anticoagulant and/or preservation fluid being is connected at manufacture or otherwise prior to the collection process. This avoids additional handling which is not time-efficient and risks impairment of the sterility of the system.

The bags and tubes in the system are produced in particular from a flexible sterilisable thermoplastic material such as polyvinyl chloride. All the tubes are in particular flexible, and able to be cut and welded.

For example, bag system 1 is sterilised and packaged in sterile packaging.

The collection device consists in particular of a needle 8 allowing access to the vein of the donor and a cap 9 protecting the needle 8. In addition, a needle protector 10 may be placed slidably on first tube 5.

First tube 5 includes downstream part 5a located between connector 6 and collection bag 4 and upstream part 5b located between collection device 2 and connector 6.

According to an embodiment depicted in FIG. 1, connector 6 is formed from a three-way junction in the form of a Y. On the two arms of the Y the downstream end of upstream part 5b of first tube 5 and the downstream end of second tube 7 are respectively connected. On the stem of the Y the upstream end of downstream part 5a of first tube 5 is connected. First and second tubes 5 and 7 are thus in fluid communication.

According to one embodiment, downstream part 5a of first tube 5 lying between connector 6 and collection bag 4 is of sufficient length to obtain a homogeneous mixture between the fluid collected and the anticoagulant and/or preservation solution before the mixture reaches the inlet orifice of collection bag 4. The length of this part 5a of first tube 5 is in particular greater than 15 cm, for example around 25 cm.

Figure 3:
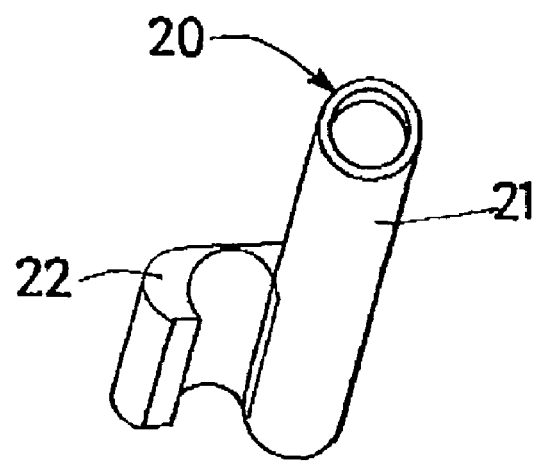
FIG. 3 depicts a perspective view of the device for associating the second tube on the first tube of a bag system according to FIG. 1.

According to one embodiment and in relation to FIGS. 1 and 3, bag system 1 includes association device 18 formed from piece 20 which is provided with object 21 for associating the device on second tube 7 and an object 22 for associating first tube 5 on piece 20.

Piece 20 includes a tubular housing forming an object 21 allowing the non-reversible fixing of the piece by inserting second tube 7 in the housing, and a lateral U-shaped housing forming an object 22 allowing the reversible fixing of first tube 5 by snapping it in the housing.

According to one embodiment, piece 20 is associated with first tube 5 by snapping downstream part 5a in the lateral housing.

According to a variant, first tube 5 is inserted in the tubular housing forming an object 21 and second tube 7 is snapped in the lateral U-shaped housing forming an object 22.

The piece may be moulded from a sterilisable plastic material, for example polycarbonate.

Piece 20 is arranged so that downstream part 7a of second tube 7, lying between connector 6 and piece 20, forms loop 19 intended to be disposed around a compression head of peristaltic pump 24.

According to one embodiment, first tube 5 may be snapped in the lateral U-shaped housing during manufacture. In a variant, the first tube may be snapped in before the collection process. This makes it possible to adapt the size of loop 19 according to the dimensions of the pump head around which the loop is intended to be disposed.

In the case where the association object of device 18 and/or of the first tube 5 are arranged so as to allow fixing, the assembly of the tubes and of piece 20 serving as association device 18 is carried out, for example, by solvent bonding.

According to another aspect depicted in FIG. 1, bag system 1 also includes a sample collection subsystem in the form of sampling bag 11 intended to receive the first millilitres of blood collected and lateral sampling device 12 associated with sampling bag 11 so as to allow the collecting of samples by means of vacuum tubes.

The sampling bag is connected by way of third tube 13 and connector 14 to upstream part 5b of first tube 5.

The samples collected using collection bag 11 must not contain any anticoagulant and/or preservation solution in order not to disrupt subsequent tests of these samples.

However, it is found that, during sterilisation of the bag systems, in particular by steam, and under the effect of the pressure created inside the system, the solutions contained in the bags in the systems discharge outside the bags in which they are normally contained.

Thus the anticoagulant and/or preservation solution may move from the solution bag 3 containing to sampling bag 11.

In order to prevent this movement during the sterilisation of the system, in particular by steam, it is advantageous to place a breakable flow obturator 15 of the circuit-opening type between bag 3 containing the anticoagulant and/or preservation solution and sampling bag 11.

In addition, it is preferable for flow obturator 15 not to be situated on the blood flow passage between collection device 2 and collection bag 4 so as to prevent any risk of hemolysis of the blood collected at the time of collection.

Circuit opener 15*a* is disposed on third tube 13 in order to block access to sampling bag 11 without interfering with the flow of fluid collected at the time of collection.

In a particular aspect, circuit opener 15*b* is disposed on upstream part 7*b* of second tube 7, in particular close to its upstream end at the outlet orifice of bag 3 containing the anticoagulant and/or preservation solution. Thus no trace of anticoagulant and/or preservation solution is situated on the flow passage between collection device 2 and sampling bag 11. The samples collected are then free from any anticoagulant and/or preservation solution and the flow of fluid collected is not interfered with.

Likewise, before use of the bag system, no trace of anticoagulant and/or preservation solution goes back up the flow path defined between collection bag 3 and collection device 2, providing exactitude of the ratio between the quantity of anticoagulant and/or preservation solution and the quantity of fluid collected.

In addition, clamps 16 and 17 may be placed on first tube 5, precisely in upstream part 5*b* of the first tube, upstream of first connector 6 and downstream of second connector 14 and/or on third tube 13, so as to control the passage of fluid in tubes 5 and 13.

According to a particular embodiment of the invention, a first optical sensor may be placed on first tube 5 between collection device 2 and connector 6, preferably between connectors 14 and 6. This sensor detects the presence of blood in order to verify that the blood is flowing suitably within tube 5. It also makes it possible to verify that there is no air or anticoagulant and/or preservation solution going back to collection device 2 and therefore to the donor. This optical sensor may for example be replaced and/or supplemented by an ultrasonic sensor making it possible to detect flow reversals more finely. A second optical sensor may be placed on second tube 7. This sensor detects the presence of anticoagulant and/or preservation solution in order to verify that the anticoagulant and/or preservation solution is flowing suitably within tube 7. These sensors are connected to control electronics provided on the collection machine.

According to a particular aspect, bag system 1 is intended for separating and filtering blood components in closed circuit. To do this the bag system also includes subsystem 29 for processing the fluid collected with an anticoagulant and/or preservation solution added.

Subsystem 29 includes one or more satellite bags 30, 31 and 32 and at least one filtration unit 33 capable in particular of retaining the leukocytes in closed circuit. Subsystem 29 is in fluid communication with collection bag 4 by way of a tube.

In a particular example depicted in FIG. 1, bag system 1 is closed and intended for filtering whole blood. Collection bag 4 is connected by way of fourth tube 34 to filtration unit 33, itself connected by way of fifth tube 35 to a bag for collecting filtrate 30.

Filtration unit 33, for example of the type described in FR-2 677 883, eliminates the leukocytes from the whole blood.

First satellite bag 31 containing a solution for preserving the red corpuscles of the SAGM type is connected by way of sixth tube 36 to filtrate collection bag 30. Second satellite bag 32 intended to receive the plasma obtained by centrifugation of the whole blood contained in filtrate collection bag 30 is in fluid communication with filtrate collection bag 30, by way of seventh tube 37, through third connector 38 placed on sixth tube 36.

In a variant which is not shown, the bag system is intended for the inactivation of the pathogens in the blood or blood components.

Figure 4:
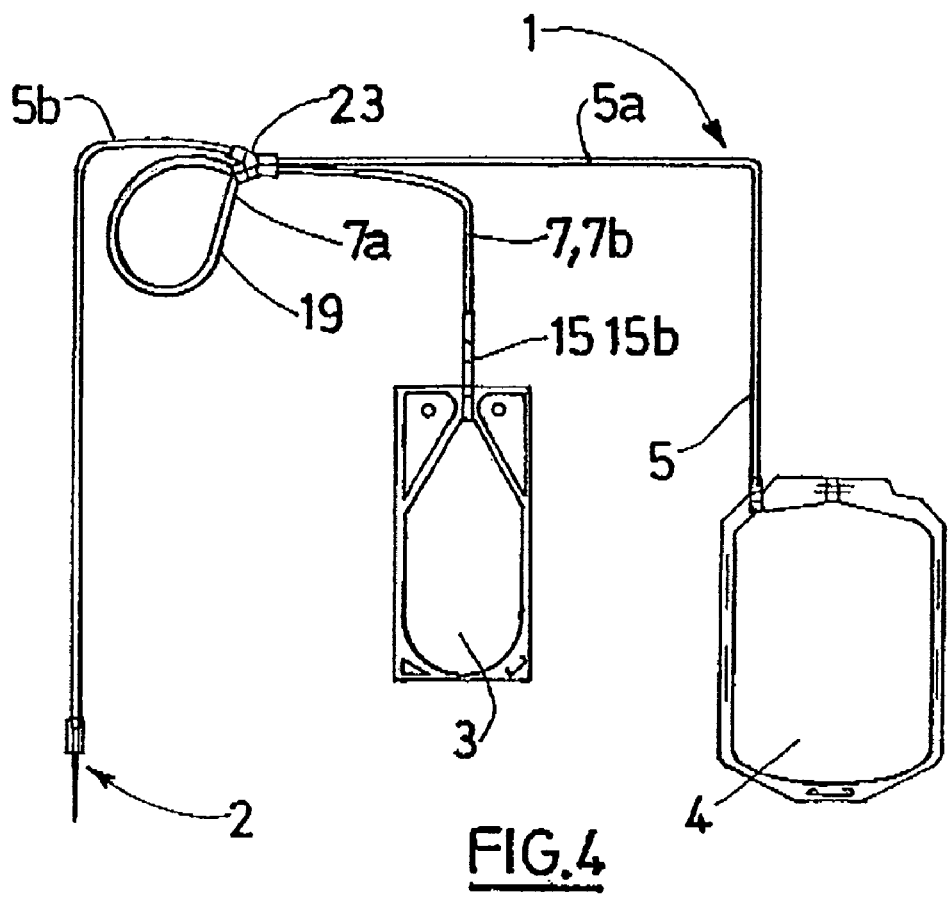
FIG. 4 depicts schematically a bag system according to a second embodiment of the invention in which the connector and association device are formed in a single piece.

According to another embodiment depicted in FIG. 4, connector 6 and association device 18 are produced in a single piece 23 corresponding to the association of a Y junction and an I junction. This piece 23 therefore forms a five-way junction with two distinct flow paths.

In this embodiment, second tube 7 consists of two tube parts, downstream part 7*a* connecting the two flow paths and upstream part 7*b* connecting bag of anticoagulant and/or preservation solution 3 to part 7*a* by way of the second flow path.

For this purpose, the downstream end of upstream part 5*b*, upstream end 10 of downstream part 5*a* and the upstream end of downstream part 7*a* are respectively connected to the three ways of the Y junction forming the first flow circuit of piece 23. In addition, the downstream end of part 7*b* and the upstream end of part 7*a* are respectively connected to the two ways of the I junction forming the second flow circuit of piece 23.

Loop 19 formed by downstream part 7*a* of second tube 7 is thus formed at the time of manufacture. The dimensions of loop 19 are then defined at the time of manufacture and remain unchanged subsequently.

Figure 2:
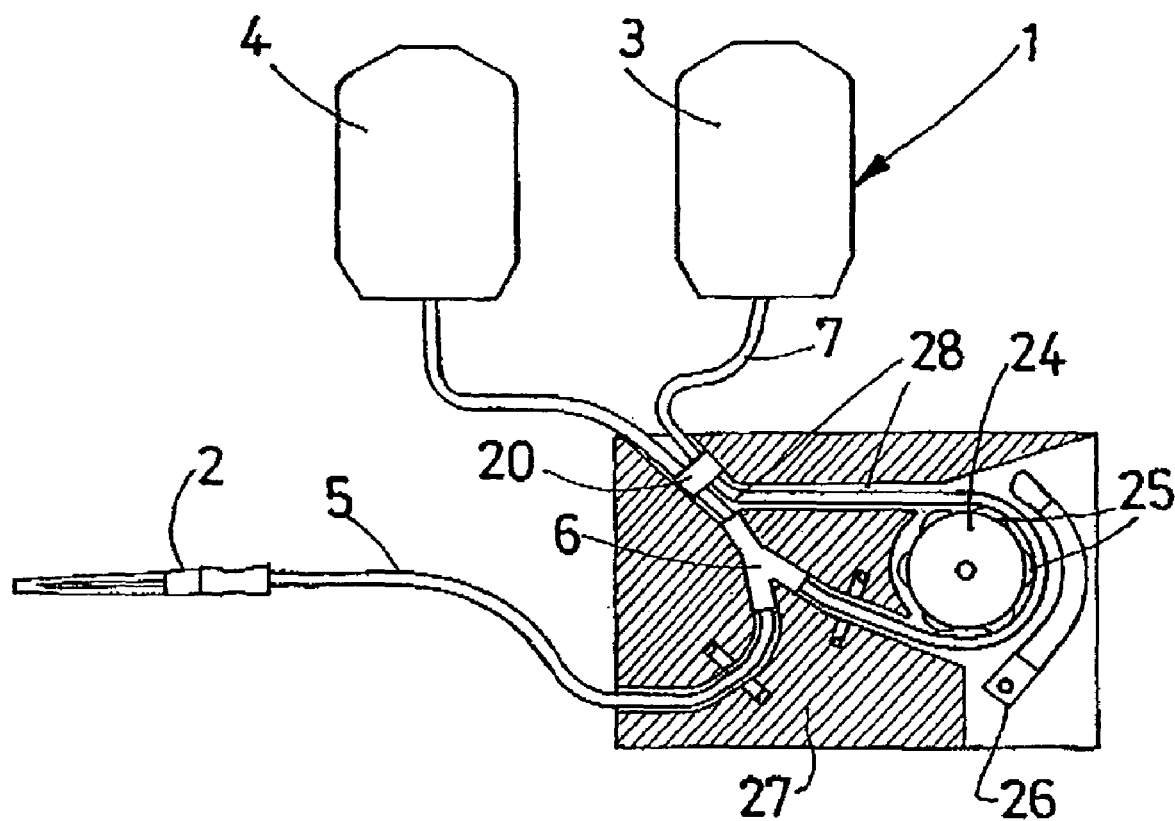
FIG. 2 depicts schematically a bag system according to another embodiment of the invention, the loop of the system being disposed in a placement device of a collection machine according to one embodiment.
Figure 5:
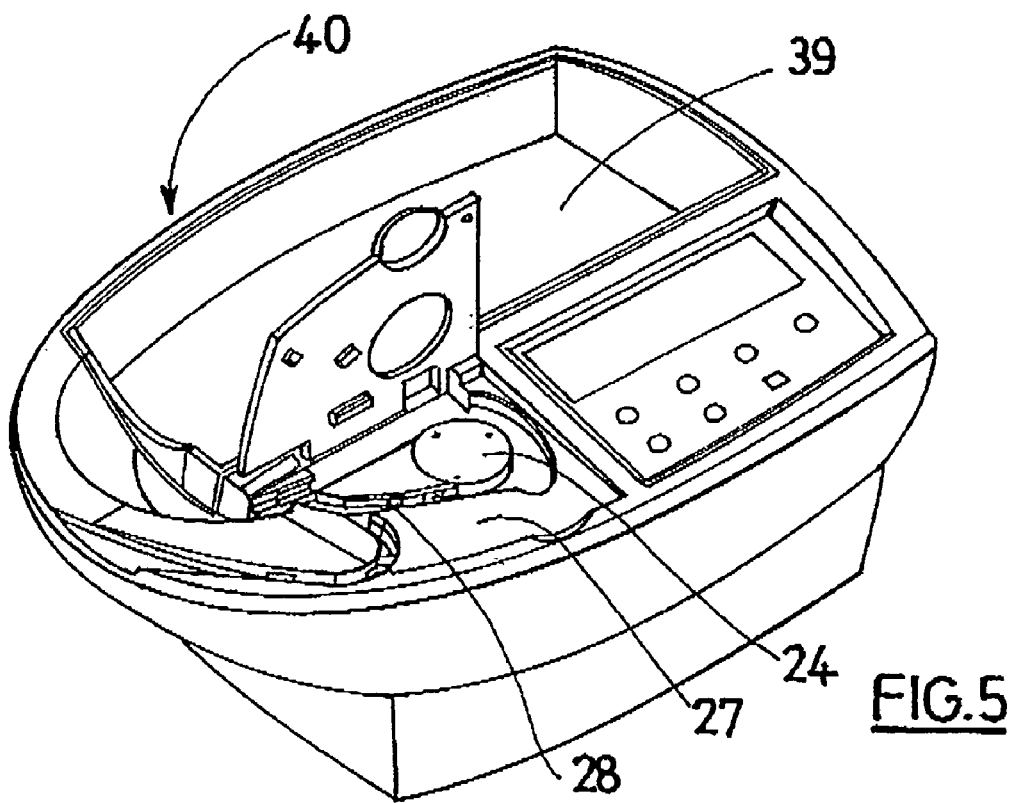
FIG. 5 depicts a schematic view in perspective of a collection machine in which a bag system according to the invention is intended to be used to allow the collection in closed circuit of a biological fluid with an anticoagulant and/or preservation solution added.

In relation to FIGS. 2 and 5, loop 19 is intended to be placed around at least part of a compression head, able to move in rotation, of peristaltic pump 24 of collection machine 40 so as to move the anticoagulant and/or preservation solution in second tube 7.

For example, collection machine 40 allows the collection of blood by natural flow, venous pressure and by gravity, providing a proportional mix between the blood collected and the anticoagulant and/or preservation solution, throughout the collection.

A collection machine, depicted in FIG. 5, includes:
  weighing device 39 including scales on which collection bag 4 alone or collection bag 4 and bag 3 of anticoagulant and/or preservation solution are placed,
  peristaltic pump 24 including a pump head causing the anticoagulant and/or preservation solution to flow in the second tube,
  control electronics (not shown) which, from the weight measurements performed by the weighing device, controls the speed of rotation of the peristaltic pump so as to obtain the required proportion by volume of anticoagulant solution to fluid collected.

When the fluid collected is blood from a donor, the ratio between the quantity of anticoagulant solution and the quantity of blood collected is in particular 1/7.

Downstream part 7*a* of the second tube forming loop 19 may have a hardness less than that of the first tube. In particular, second tube 7 has a hardness of between 60 and 70

Shore A, in particular 65 Shore A. The other tubes have a hardness greater than 70 Shore A, in particular 78.

When peristaltic pump 24 is in movement, the rollers of pump head 24 successively compress the section of second tube 7 against curved device 26 so as to provide the movement of the anticoagulant and/or preservation solution.

As depicted in FIGS. 2 and 5, the pump head is included in area 27 for assisting the placement of the tubes. This area 27 includes groove 28 arranged to house the part of loop 19 which is not disposed around the head. Groove 28 is also provided with housings for housing association device 18 and first connector 6.

The geometry of the housings is arranged so as to allow locking of the connector and association device in groove 28 so that second tube 7 is not moved by the rotation of pump head 24 when in operation. In particular, in order to obtain this locking, it may be desirable to have a fixed association between first tube 5 and association device 18.

The immobilisation of second tube 7 makes it possible to obtain an even flow inside the second tube 7 and optimum functioning of peristaltic pump 24.

Preformed loop 19 combined with first connector 6 and association device 18 also serves as a foolproof location device because it obliges the user to place bag system 1 in a given correct orientation because groove 28 is arranged so as to allow the placement of the loop in a single direction.

What is claimed is:

1. A bag system comprising:
   a collection machine including a peristaltic pump;
   a collection device operable to collect a biological fluid;
   a solution bag containing an anticoagulant and/or preservation solution;
   a collection bag operable to receive the biological fluid collected and the anticoagulant and/or preservation solution;
   a first flexible tube providing fluid communication between the collection device and the collection bag;
   a second flexible tube providing fluid communication between the solution bag and the collection bag; and
   an association device comprising a five-way junction, the five-way junction having a Y junction and an I junction and connecting at least the first and second flexible tubes, the association device forming a loop with the second flexible tube between the I junction and the Y junction;
   wherein the loop has a conformation operable to allow its disposition around a head of the peristaltic pump; and
   wherein the system has a closed circuit.

2. The system of claim 1, further comprising the association device molded from a sterilizable plastics material.

3. The system of claim 1, further comprising a circuit opener disposed near an upstream end of the second tube.

4. The system of claim 1, further comprising the length of the first tube between the connector Y junction and an inlet orifice of the collection bag greater than 15 cm.

5. The system of claim 1, further comprising a part of the second tube forming the loop having a hardness less than that of the first tube.

6. The system of claim 1, further comprising a subsystem including:
   at least one satellite bag;
   at least one filter; and
   a third tube providing fluid communication between the satellite bag and the collection bag.

7. The system of claim 1, further comprising a subsystem operable to allow sampling of the biological fluid disposed on the first tube upstream of the connector.

* * * * *